(12) United States Patent
West et al.

(10) Patent No.: US 7,579,140 B2
(45) Date of Patent: Aug. 25, 2009

(54) METHOD AND REAGENT FOR MEASURING NITROREDUCTASE ENZYME ACTIVITY

(75) Inventors: Richard Martin West, Whitechurch (GB); Rahman Aziz Ismail, Whitechurch (GB)

(73) Assignee: GE Healthcare UK Limited, Amersham (GB)

( * ) Notice: Subject to any disclaimer, the term of this patent is extended or adjusted under 35 U.S.C. 154(b) by 367 days.

(21) Appl. No.: 11/569,682

(22) PCT Filed: May 24, 2005

(86) PCT No.: PCT/GB2005/002057

§ 371 (c)(1),
(2), (4) Date: Nov. 28, 2006

(87) PCT Pub. No.: WO2005/118839

PCT Pub. Date: Dec. 15, 2005

(65) Prior Publication Data
US 2008/0317674 A1    Dec. 25, 2008

(30) Foreign Application Priority Data
May 28, 2004    (GB) ................................. 0411993.9

(51) Int. Cl.
*C12Q 1/00* (2006.01)
(52) U.S. Cl. ........................................................ 435/4
(58) Field of Classification Search ...................... None
See application file for complete search history.

(56) References Cited

U.S. PATENT DOCUMENTS 6,403,807 B1   6/2002   Singh et al.
2003/0186348 A1   10/2003   Thomas et al.

FOREIGN PATENT DOCUMENTS

| EP | 0645680 | 3/1995 |
| WO | WO97/40104 | 10/1997 |
| WO | WO03/087052 | 11/2006 |

OTHER PUBLICATIONS

James et al. "Fluorogenic substrates for the detection of microbial nitroreductases", Letters in Applied Microbiology, 2001, 33:403-408.*

Kuthanapillil, J., et al., "Synthesis of Novel Quinaldine-Based Squarine Dyes: Effect of Substituents and Role of Electronic Factors", Organic Letters, vol. 6, No. 22, 2004, p. 3965-3968.
Lin, T., et al., "Synthesis and Spectral Characteristics of Some Highly Soluble Squarylium Cyanine Dyes", Dyes and Pigments, vol. 35, No. 4, 1997, p. 331-338.

* cited by examiner

Primary Examiner—Jon P Weber
Assistant Examiner—Bin Shen
(74) Attorney, Agent, or Firm—Jonggang Ji (57) ABSTRACT

Disclosed are nitro-substituted squaraine reporter dyes and methods using such dyes for detecting nitroreductase enzyme activity and nitroreductase gene expression in cellular assays. The dyes are of the structure:

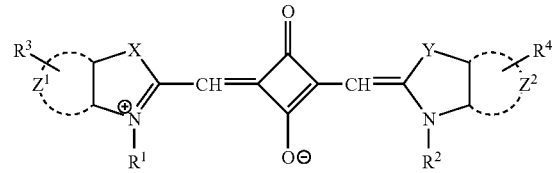

in which $Z^1$ and $Z^2$ independently represent a phenyl or a naphthyl ring system; X and Y are selected from oxygen, sulphur, —CH=CH— and the group:

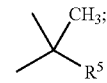

$R^1$ and $R^2$ are selected from $C_1$-$C_4$ alkyl, —$(CH_2)_n$—P, —{$(CH_2)_2$—O}$_p$—$R^6$ and group W; where P is selected from $COOR^7$, $SO_3^-$ and OH, W is mono- or di-substituted nitrobenzyl, $R^6$ is methyl or ethyl, $R^7$ is selected from H, $C_1$-$C_4$ alkyl and $CH_2OC(O)R^8$, where $R^8$ is methyl, or t-butyl, n is an integer from 1 to 10, and p is an integer from 1 to 3; $R^3$ and $R^4$ are selected from hydrogen, $NO_2$, halogen, $SO_3^-$, $C_1$-$C_4$ alkoxy and —$(CH_2)_m$—$COOR^7$; where $R^7$ is hereinbefore defined and m is 0 or an integer from 1 to 5; $R^5$ is $C_1$-$C_6$ alkyl optionally substituted with $COOR^7$, $SO_3^-$, or OH; where $R^7$ is hereinbefore defined; and at least one of groups $R^1$, $R^2$, $R^3$ and $R^4$ comprises at least one $NO_2$ group. Also provided are methods for screening for a test agent whose effect upon nitroreductase enzyme activity and nitroreductase gene expression is to be determined.

14 Claims, 5 Drawing Sheets

Nitro-substituted Cyanine Dye Nitroreductase Substrates:

Compounds (i) and (iii)

Figure 1a

Compound (i)

Figure 1b

Compound (iii)

Comparison of two nitro-substituted cyanine type dyes, Compounds (i) and (iii) compared with a nitro-substituted squaraine dye (Compound (1))

Figure 2a    Fluorescence emission

Figure 2b    Signal:Background

A Comparative Study of Nitro-substituted Squaraine Dyes (Compounds (1) and 2) as Substrates in a Nitroreductase Gene Reporter Assay Figure 3a    Fluorescence emission Figure 3b    Signal:Background Distribution of Compound (2) in HeLa cells

Figure 4

Evaluation of Compounds (2), (3) and (4) as Nitroreductase Substrates in live cell NTR assays Figure 5a    Fluorescence emission Figure 5b    Signal:Background

METHOD AND REAGENT FOR MEASURING NITROREDUCTASE ENZYME ACTIVITY

CROSS REFERENCE TO RELATED APPLICATIONS

This application is a filing under 35 U.S.C. §371 and claims priority to international patent application number PCT/GB2005/002057 filed May 24, 2005, published on Dec. 15, 2005, as WO 2005/118839, which claims priority to patent application number 0411993.9 filed in Great Britain on May 28, 2004; the disclosure of which is incorporated herein by reference in its entirety.

FIELD OF THE INVENTION

The present invention relates to the field of enzyme assays. In particular, the invention relates to nitroreductase enzyme assays and new reporter dyes for measuring nitroreductase enzyme activity and nitroreductase gene expression in cell based systems.

BACKGROUND OF THE INVENTION

Reporter gene technology is widely used to monitor cellular events associated with signal transduction and gene expression. Transcriptional regulation, coupled to the expression of a reporter gene is routinely used to monitor a wide variety of cellular events. To establish a reporter gene assay, the reporter gene is placed under the transcriptional control of a promoter or an enhancer with a minimal promoter. The reporter is inserted into a suitable plasmid vector typically containing a selectable marker that confers resistance to growth suppressing compounds, such as antibiotics. The vector DNA is introduced into cells using standard laboratory procedures. Addition of a suitable agonist will switch on the cell signalling pathway, leading to activation of a transcription factor and gene expression. A review of reporter gene technology is given by Naylor et al, in Biochem. Pharmacol., (1999), 58, 749-757.

A cell-based fluorescent gene reporter system has been described, the assay employing bacterial nitroreductase (NTR) and a cell permeable nitro-substituted quenched (or non-fluorescent) cyanine dye (shown as Compound (i)), which functions as a substrate for the enzyme (US 2003/0186348, Thomas, N. et al).

Cellular uptake of the substrate, by passive diffusion across the plasma membrane, was promoted through the use of ethyl ester groups to mask latent polar functionality. Intracellular cleavage of the ester groups by cellular hydrolases results in retention of the substrate inside live cells. Addition of the substrate to a cell that is expressing nitroreductase results in the reduction of the nitro group to the hydroxylamine with a concomitant increase in fluorescence emission. Depending on the structure of the quenched cyanine dye, the fluorescence emission from the product of the NTR reaction may be generated across a wide range of wavelengths, typically 500-900 nm. Emission at longer wavelengths is advantageous in avoiding background fluorescence and increasing sensitivity in biological systems.

Wild type nitroreductase expressed from a reporter construct is localised in the cytoplasm of the host cell (Spooner et al, Int. J. Cancer, (2001), 93, 123-30). To achieve a maximum signal output from the assay it is desirable to localise the substrate to the same cellular compartment as the reporter enzyme, i.e. within the cytoplasm of the host cell such that the substrate is available for activation by nitroreductase. The masking of hydrophilic groups on, or attached to, the substrate molecule can generate membrane permeable compounds. Furthermore, the masking group can be designed to cleave from the substrate within the cell to generate the substrate intracellularly, preferably within the cytoplasm of the cell. Masking strategies to enable delivery of nitro-substituted cyanine dyes relatively uniformly to the cell cytoplasm have not proved to be entirely successful. A study of the localisation of cell permeant quenched cyanine dye (Cy-Q) derivatives within cells using fluorescence microscopy, has shown the localisation of some of the substrate to internal cell membranes and organelles, predominantly the mitochondria of the cell. Accumulation of lipophilic, cationic nitro-substituted cyanine dye substrates within mitochondria is accompanied by an increase in fluorescence of the probe and this accumulation results in an increase in background fluorescence in NTR assays. Thus, there is a need for new and improved reagents for use as NTR substrates that display lower background fluorescence, improved fluorescence signal and cellular distribution.

Squarylium (squaraine) dyes are a class of dyes that have overall electrical neutrality; an example is shown as Compound (ii).

Compound (ii)

Compound (i)

Nitro-substituted squaraine dyes are known from EP 645680 (Bugner D., et al) as near infra-red absorbing additives for use in electrophotographic imaging processes. PCT Application No. WO97/40104 (Hamilton, A. L. et al) discloses squaraine dyes and adducts of squaraine dyes with biological molecules such as peptides, proteins and nucleotides. The dyes may be substituted by electron donating and electron withdrawing substituents, for example nitro; however, the fluorescence properties of the nitro-substituted dyes are not disclosed. The present inventors have now discovered that nitro-group-containing quenched squaraine dyes are effective substrates for nitroreductase through reduction of the nitro group, resulting in a change in an optical property, preferably a change in fluorescence emission, of the squaraine dye. Use of nitro-substituted squaraine dyes in assays for determining nitroreductase activity results in greater sensitivity and lower background fluorescence than in assays that employ conventional NTR substrates.

BRIEF DESCRIPTION OF THE INVENTION

In a first aspect of the invention, there is provided a method for detecting nitroreductase enzyme activity in a composition comprising:
i) mixing said composition under conditions to promote nitroreductase activity with a dye molecule; and
ii) measuring a change in an optical property of said dye molecule wherein said change is a measure of the amount of nitroreductase activity; characterised in that said dye molecule is a squaraine dye comprising at least one $NO_2$ group.

In one embodiment, the composition in which nitroreductase enzyme activity is to be detected comprises at least one cell or a cell extract. The cell may be ex-vivo, or in-vivo. For example, the cell may be cultured under standard laboratory conditions, or the composition may be a live animal cell.

In another embodiment, the method is conducted in the presence of a test agent whose effect on nitroreductase enzyme activity is to be determined.

In a second aspect of the invention there is provided a method which comprises:
i) contacting a host cell with a dye molecule wherein said host cell has been transfected with a nucleic acid molecule comprising expression control sequences operably linked to a sequence encoding a nitroreductase; and
ii) measuring a change in an optical property of said dye molecule wherein said change is a measure of the amount of nitroreductase activity;

characterised in that said dye molecule is a squaraine dye comprising at least one $NO_2$ group.

The optical property that is measured in the dye molecule is suitably the fluorescence emission intensity, such that there is an increase in fluorescence emission as a result of the action of the enzyme upon the dye. For example, the composition may be excited at a first wavelength, suitably the excitation maximum of the dye, and the fluorescence emission intensity measured at a second wavelength corresponding to the emission maximum of the product of the enzyme reaction. Excitation of the dye molecule and measurement of fluorescence emission may also be over a range of wavelengths, so as to maximise emission signal and to distinguish between excitation and emission signals. Alternatively, the measured change in an optical property may be a change in fluorescence lifetime of the dye, before and after the action of the nitroreductase enzyme. The change in fluorescence lifetime may also be used to distinguish the product of the enzyme reaction from the dye molecule used as the substrate. As a further alternative, the change in an optical property may be a change in the absorption maximum of the dye molecule, relative to the absorption maximum of the product. In preferred embodiments, the change in an optical property is an increase in the fluorescence intensity of the dye molecule, whereby the increase is a measure of the amount of nitroreductase activity.

Suitably, the squaraine dye according to the first and second aspects is a compound of formula (I):

(I)

wherein:
$R^3$ is attached to the $Z^1$ ring structure and $R^4$ is attached to the $Z^2$ ring structure;
$Z^1$ and $Z^2$ independently represent a phenyl or a naphthyl ring system;
X and Y are the same or different and are selected from oxygen, sulphur, —CH=CH— and the group:

groups $R^1$ and $R^2$ are independently selected from $C_1$-$C_4$ alkyl, —$(CH_2)_n$—P, —{$(CH_2)_2$—O}$_p$—$R^6$ and the group W; where P is selected from $COOR^7$, $SO_3^-$ and OH, W is mono- or di-substituted nitrobenzyl, $R^6$ is methyl or ethyl, $R^7$ is selected from H, $C_1$-$C_4$ alkyl and $CH_2OC(O)R^8$, where $R^8$ is methyl, or t-butyl, n is an integer from 1 to 10, and p is an integer from 1 to 3;
groups $R^3$ and $R^4$ are independently selected from hydrogen, $NO_2$, halogen, $SO_3^-$, $C_1$-$C_4$ alkoxy and —$(CH_2)_m$—$COOR^7$; where $R^7$ is hereinbefore defined and m is 0 or an integer from 1 to 5;
$R^5$ is $C_1$-$C_6$ alkyl optionally substituted with $COOR^7$, $SO_3^-$, or OH; where $R^7$ is hereinbefore defined; and
at least one of groups $R^1$, $R^2$, $R^3$ and $R^4$ comprises at least one $NO_2$ group.

Suitably, the squaraine dye of formula (I) may include a counter-ion, which may be positive or negative to balance the formal charge (or charges) on the dye chromophore or on substituent groups. The nature of the counter-ion is not material to the invention and could be one of many known ions such as $H^+$, $NH_4^+$, $K^+$, $Na^+$, trifluoroacetate ($F_3C$—$CO_2^-$), perchlorate ($ClO_4^-$), $Br^-$, or $I^-$.

Suitably, the at least one nitro group comprised in the dyes of formula (I), may be attached directly to the $Z^1$ and $Z^2$ ring structures. In this embodiment, one or both of groups $R^3$ and $R^4$ of the squaraine dye are $NO_2$. In an alternative embodiment, one or both of groups $R^1$ and $R^2$ of said squaraine dye are the group W, where W is hereinbefore defined. The squaraine dye may optionally be further substituted with one or two nitro groups attached to the aromatic ring structures.

In preferred embodiments, the squaraine dye employed in the methods according to the invention is permeable to cells. In these embodiments, at least one of groups $R^1$, $R^2$, $R^3$ and $R^4$ comprises a cell membrane permeabilising group. Membrane permeant compounds can be generated by masking hydrophilic groups to provide more hydrophobic compounds. The masking groups can be designed to be cleaved from the substrate within the cell to generate the derived substrate intracellularly. Since the substrate is more hydrophilic than the membrane permeant derivative, it is trapped within the cell. Suitable cell membrane permeabilising groups may be selected from acetoxymethyl ester which is readily cleaved by endogenous mammalian intracellular esterases (Jansen, A. B. A. and Russell, T. J., J. Chem. Soc., 2127-2132 (1965) and Daehne, W. et al. J. Med-. Chem. 13, 697-612 (1970)) and pivaloyl ester (Madhu et al., J. Ocul. Pharmacol. Ther., (1998), 14, 5, pp 389-399), although other suitable groups will be recognised by those skilled in the art.

In one embodiment, one or both of groups $R^1$ and $R^2$ of the squaraine dye is the group W, where W is hereinbefore defined. Particular examples of dyes utilised in this embodiment of the methods of the invention are those selected from dyes of formula (II), (III) and (IV):

wherein:

X and Y are the same or different and are selected from oxygen, sulphur, —CH=CH— and the group:

wherein $R^5$ is hereinbefore defined;

at least one of groups $R^1$ and $R^2$ is the group W; where W is hereinbefore defined;

any remaining group $R^1$ or $R^2$ is selected from $C_1$-$C_4$ alkyl, —$(CH_2)_n$—P and —$\{(CH_2)_2$—O$\}_p$—$R^6$; where P is selected from $COOR^7$, $SO_3^-$ and OH, $R^6$ is methyl or ethyl, $R^7$ is selected from H, $C_1$-$C_4$ alkyl and $CH_2OC(O)R^8$, where $R^8$ is methyl, or t-butyl, n is an integer from 1 to 10 and p is an integer from 1 to 3; and groups $R^3$ and $R^4$ are independently selected from hydrogen, halogen, $SO_3^-$, $C_1$-$C_4$ alkoxy and —$(CH_2)_m$—$COOR^7$; where $R^7$ is hereinbefore defined and m is 0 or an integer from 1 to 5.

In this embodiment, preferably one of groups $R^1$ and $R^2$ is selected from group W where W is selected from:

remaining $R^1$ or $R^2$ is selected from methyl and ethyl, or is the group —$(CH_2)_n$—$COOR^7$ where $R^7$ is selected from H, $C_1$-$C_4$ alkyl and $CH_2OC(O)R^8$, where $R^8$ is methyl, or t-butyl, n is an integer from 1 to 10, preferably 5 or 6. In a particularly preferred embodiment, W is the group:

and remaining $R^1$ or $R^2$ is hereinbefore defined.

In an alternative embodiment, one or both of groups $R^3$ and $R^4$ of the squaraine dye according to formula (II), (III) and (IV) are $NO_2$. In this embodiment, X and Y are the same or different and are selected from oxygen, sulphur, —CH=CH— and the group:

wherein $R^5$ is hereinbefore defined;

groups $R^1$ or $R^2$ are independently selected from $C_1$-$C_4$ alkyl, —$(CH_2)_n$—P and —$\{(CH_2)_2$—O$\}_p$—$R^6$; where P is selected from $COOR^7$, $SO_3^-$ and OH, $R^6$ is methyl or ethyl, $R^7$ is selected from H, $C_1$-$C_4$ alkyl and $CH_2OC(O)R^8$, where $R^8$ is methyl, or t-butyl, n is an integer from 1 to 10 and p is an integer from 1 to 3;

at least one of groups $R^3$ and $R^4$ is $NO_2$; and any remaining group $R^3$ or $R^4$ is selected from hydrogen, $SO_3^-$, $C_1$-$C_4$ alkoxy and —$(CH_2)_m$—$COOR^7$; where $R^7$ is selected from H, $C_1$-$C_4$ alkyl and $CH_2OC(O)R^8$, where $R^8$ is methyl, or t-butyl, and m is 0 or an integer from 1 to 5.

In preferred embodiments X and Y are selected from oxygen, sulphur and where $R^5$ is methyl.

Preferred $C_1$-$C_4$ alkyl groups are selected from methyl and ethyl. A particularly preferred —$(CH_2)_n$—$COOR^7$, group is selected from —(CH$_2$)$_5$—COOR$^7$ and —(CH$_2$)$_6$—COOR$^7$; where R$^7$ is hereinbefore defined.

Halogen atoms are selected from fluorine, chlorine, bromine and iodine.

In a third aspect there is provided a method for screening for a test agent whose effect upon nitroreductase gene expression is to be determined. The method comprises the steps of: a) performing the method according to the second aspect in the absence and in the presence of said test agent; and b) determining the amount of nitroreductase gene expression in the absence and in the presence of said agent; wherein a difference between the amount of nitroreductase gene expression in the absence and in the presence of said agent is indicative of the effect of said agent on nitroreductase gene expression.

In an alternative aspect, the method for screening for a test agent may be conducted by a) performing the method according to the second aspect in the presence of said agent; and b) comparing the amount of nitroreductase gene expression with a control value for the amount of nitroreductase gene expression in the absence of the test agent. The control values may be stored electronically in a database or other electronic format.

Methods for using a variety of enzyme genes as reporter genes in mammalian cells are well known (for a review see Naylor L. H. (1999) Biochemical Pharmacology 58, 749-757). The reporter gene is chosen to allow the product of the gene to be measurable in the presence of other cellular proteins and is introduced into the cell under the control of a chosen regulatory sequence which is responsive to changes in gene expression in the host cell. Typical regulatory sequences include those responsive to hormones, second messengers and other cellular control and signalling factors. For example, agonist binding to seven transmembrane receptors is known to modulate promoter elements including the cAMP responsive element, NFAT, SRE and AP1; MAP kinase activation leads to modulation of SRE leading to Fos and Jun transcription; DNA damage leads to activation of transcription of DNA repair enzymes and the tumour suppressor gene p53. By selection of an appropriate regulatory sequence the reporter gene can be used to assay the effect of added agents on cellular processes involving the chosen regulatory sequence under study.

For use as a reporter, the nitroreductase gene may be isolated by well known methods, for example by amplification from a cDNA library by use of the polymerase chain reaction (PCR) (Molecular Cloning, A Laboratory Manual 2$^{nd}$ Edition, Cold Spring Harbour Laboratory Press 1989 pp 14.5-14.20). Once isolated, the nitroreductase gene may be inserted into a vector suitable for use with mammalian promoters (Molecular Cloning, A Laboratory Manual 2$^{nd}$ Edition, Cold Spring Harbour Laboratory Press 1989 pp 16.56-16.57) in conjunction with and under the control of the gene regulatory sequence under study. The vector containing the nitroreductase reporter and associated regulatory sequences may then be introduced into the host cell by transfection using well known techniques, for example by use of DEAE-Dextran or Calcium Phosphate (Molecular Cloning, A Laboratory Manual 2$^{nd}$ Edition, Cold Spring Harbour Laboratory Press 1989 pp 16.30-16.46). Other suitable techniques will be well known to those skilled in the art. Nitroreductase has been shown to be retained in cells when expressed in this manner (see Bridgewater et al., Eur. J. Cancer, (1995), 31A, 2362-70).

The methods of the invention may be used with any adherent cell type that can be cultured on standard tissue culture plastic-ware, including cell types derived from any recognised source with respect to species (e.g. human, rodent, simian), tissue source (e.g. brain, liver, lung, heart, kidney skin, muscle) and cell type (e.g. epithelial, endothelial). There are established protocols available for the culture of diverse cell types. (See for example, Freshney, R. I., Culture of Animal Cells: A Manual of Basic Technique, 2$^{nd}$ Edition, Alan R.Liss Inc. 1987). The chosen host cell line is seeded into sterile, tissue culture treated dishes and incubated at 37° C. in an humidified atmosphere of 5% CO$_2$ in a suitable medium, typically Dulbecco's Modified Eagles medium containing 10% foetal calf serum +2 mM L-glutamine. Transfection of the plasmid vector into mammalian cells may be achieved using well known methods, e.g. by the use of cationic lipids, calcium phosphate, and electroporation. It is recommended that transfection efficiencies are optimised for each cell line prior to testing to ensure that reproducible data are obtained. Transient expression of nitroreductase is typically assayed 24-72 hours post transfection. The prepared nitroreductase gene reporter DNA/transfection reagent complex is added in a dropwise manner to each dish. The contents of the dish are carefully mixed and incubated for a minimum of 4 hours. Overnight incubation at 37° C. in a humidified atmosphere of 5% CO$_2$ is convenient. Following incubation, medium is removed from each dish and the cell monolayer washed with sterile phosphate buffered saline (PBS). Transfected cells may be assayed directly in the transfection dish, or alternatively cells may be detached from each dish pooled to produce a suspension of transfected cells. Transient expression of nitroreductase is typically assayed 24-72 hours post transfection.

In a typical adenoviral based NTR gene reporter assay according to the invention, the chosen host cell line is subcultured twenty-four hours prior to viral transduction and incubated overnight at 37° C. in a humidified atmosphere of 5% CO$_2$. Cells are detached with trypsin and cells from each flask pooled to produce a suspension of cells. Cells in suspension are combined with virus at a predetermined multiplicity of infection (MOI) in a sufficient volume of complete medium to cover the base of a suitable tissue culture treated flask and incubated overnight at 37° C. in a humidified atmosphere of 5% CO$_2$. Cells are detached (trypsin) to produce a suspension of transduced cells.

Suitably, the nitroreductase containing vector may be used to produce both transient and stable cells for use in gene reporter assays. For stable cell line production, selection with a suitable reagent, such as the antibiotic G418 is necessary. According to this procedure, cells should be seeded at a low density, suitably 100-500 into a suitable dish, and the selection agent added to the medium. The optimum concentration of selection agent will vary according to the cell type and growth rate required and is suitably added at a concentration of between 0.1 mg/ml and 1 mg/ml.

For the assay of the effect of a test agent on nitroreductase activity, cells are dispensed in the wells of a microwell plate, suitably a microtitre plate having 24, 96, 384 or higher densities of wells, e.g. 1536 wells. Following overnight incubation at 37° C., medium is removed and the test agent is added in serum free medium. Wells containing serum free medium only are used as the control. Following incubation, the nitroreductase substrate is added and the fluorescent signal increase is measured over time using a suitable fluorimeter or imaging system.

To assay the activity of a test agent to activate cellular responses via the regulatory sequence under study, cells that have been transfected with the nitroreductase reporter are incubated with the test agent, followed by addition of a cell-permeant squaraine dye substrate, such as a squaraine dye comprising at least one $NO_2$ group. After an appropriate period required for conversion of the dye substrate to a form emitting increased fluorescence, the fluorescence emission from the cells is measured over time at a wavelength appropriate for the chosen squaraine dye, using a suitable fluorimeter or imaging system.

Typically, gene reporter assays are performed under "stopped" conditions, e.g. lysis of cells for detection of reporter gene. Thus, the reaction is allowed to proceed for a predetermined time and then terminated with a stop reagent, normally a surfactant. An example of a stop reagent is Triton X-100, which is used to disrupt cell membranes and release the enzymatic activity. In addition, cells may be "fixed" using standard reagents, such as formaldehyde, and the product of the nitroreductase reaction retained within the cell. This allows storage of assay plates until a suitable time for reading is available.

Where an assay is to be formatted for the determination of the activity of a test agent on nitroreductase activity, the assay may be performed under continuous measurement of the fluorescence of the substrate. In this format, the fluorescence emission intensity of the substrate changes continuously. A time-course of the reaction may be obtained, allowing kinetic studies to be performed in real time. Measurements of emitted fluorescence may be compared with fluorescence measurements from control cells not exposed to the test agent and the effects, if any, of the test agent on gene expression modulated through the regulatory sequence is determined from the ratio of fluorescence in the test cells to the fluorescence in the control cells.

Measurements of changes in fluorescence intensity may be made using instruments incorporating photo-multiplier tubes as detectors, for example an "Ultra" fluorimeter (Tecan), or by means of a charge coupled device (CCD) imager (such as a scanning imager or an area imager) to image all of the wells of a microtitre plate. The LEADseeker™ system features a CCD camera allowing fluorescence imaging of high density microtitre plates in a single pass. Imaging is quantitative and fast, and instrumentation suitable for imaging applications can now simultaneously image the whole of a multiwell plate. Alternatively, cells may be imaged in "live cell" format using an INCell™ 1000 Analyzer or INCell™ 3000 Analyzer. In this format, a suitable cell marker should be introduced into the cell, such as a cytosolic, nuclear or membrane fluorescent label having a fluorescence emission wavelength that is different and distinguishable from the fluorescence emission of the reduced substrate. Suitably, the increase in fluorescence emitted by the substrate is detected at a wavelength in the range 500 nm to 900 nm, preferably 550-780 nm, and, most preferably 630-700 nm. For example, for Compound (1) (Example 1), the fluorescence emission may be monitored at 645 nm with excitation at 630 nm. Alternatively, the dye may be administered in vivo to a suitably engineered transgenic animal model. Nitroreductase activity and localisation may then be determined by imaging with a suitable optical system, for example, the eXplore Optix™.

In a further aspect, the present invention provides nitro-substituted squaraine dyes selected from dyes of formula:

wherein:

X and Y are the same or different and are selected from oxygen, sulphur, —CH═CH— and the group:

groups $R^1$ and $R^2$ are independently selected from $C_1$-$C_4$ alkyl, —$(CH_2)_n$—P, —$\{(CH_2)_2$—O$\}_p$—$R^6$ and the group W; where P is selected from COOR, $SO_3^-$ and OH, W is mono- or di-substituted nitrobenzyl, $R^6$ is methyl or ethyl, $R^7$ is selected from H, $C_1$-$C_4$ alkyl and $CH_2OC(O)R^8$, where $R^8$ is methyl, or t-butyl, n is an integer from 1 to 10, and p is an integer from 1 to 3;

groups $R^3$ and $R^4$ are independently selected from hydrogen, $NO_2$, halogen, $SO_3^-$, $C_1$-$C_4$ alkoxy and —$(CH_2)_n$—$COOR^7$; where $R^7$ is selected from H, $C_1$-$C_4$ alkyl and $CH_2OC(O)R^8$, where $R^8$ is methyl, or t-butyl, and m is 0 or an integer from 1 to 5;

$R^5$ is $C_1$-$C_6$ alkyl optionally substituted with $COOR^7$, $SO_3^-$, or OH; where $R^7$ is hereinbefore defined; and at least one of groups $R^1$, $R^2$, $R^3$ and $R^4$ comprises at least one $NO_2$ group.

Preferably, X and Y are selected from oxygen, sulphur and where $R^5$ is methyl.

In one embodiment, one of groups $R^1$ and $R^2$ is remaining $R^1$ or $R^2$ is selected from methyl, ethyl and the group $-(CH_2)_n-COOR^7$;
where $R^7$ is hereinbefore defined and n is an integer from 1 to 10, preferably 5 or 6.

In an alternative embodiment, groups $R^1$ and $R^2$ are independently selected from $C_1$-$C_4$ alkyl, $-(CH_2)_n-COOR^7$ and $-\{(CH_2)_2-O\}_p-R^6$; where $R^6$ is methyl or ethyl, $R^7$ is selected from H, $C_1$-$C_4$ alkyl and $CH_2OC(O)R^8$, where $R^8$ is methyl, or t-butyl, and n and p are hereinbefore defined;
at least one of groups $R^3$ and $R^4$ is $NO_2$; and
remaining group $R^3$ or $R^4$ is selected from hydrogen, $SO_3^-$, $C_1$-$C_4$ alkoxy and $-(CH_2)_m-COOR^7$; where $R^7$ is hereinbefore defined and m is 0 or an integer from 1 to 5.

The squaraine dyes are useful as substrates for the detection and/or measurement of nitroreductase enzyme activity and in particular for measuring the amount of nitroreductase gene expression in cellular assays.

Examples of dyes according to the first aspect of the invention are as follows:
i) 2-(1-methyl-3,3-dimethyl-2-indolinylidenemethyl)-4-(1-(3,5-dinitrobenzyl)-3,3-dimethyl-2-indolinylidenemethyl)cyclobutenediylium-1,3-diolate (Compound 1);
ii) 2-(1-(5-carboxypentyl)-3,3-dimethyl-2-indolinylidenemethyl)-4-(1-(3,5-dinitrobenzyl)-3,3-dimethyl-2-indolinylidenemethyl)cyclobutenediylium-1,3-diolate (Compound 2);
iii) 2-(1-(5-carboxypentyl)-3,3-dimethyl-2-benzindolinylidenemethyl)-4-(1-(3,5-dinitrobenzyl)-3,3-dimethyl-2-indolinylidenemethyl)cyclobutenediylium-1,3-diolate (Compound 3);
iv) 2-(3-ethyl-6-nitro-2-benzothiazolinylidenemethyl)-4-(1-(2-(2-methoxyethoxy)ethyl)-3,3-dimethyl-2-indolinylidenemethyl)cyclobutenediylium-1,3-diolate (Compound 4);
v) 2-(1-ethyl-3,3-dimethyl-5-methoxy-2-indolinylidenemethyl)-4-(1-(3,5-dinitrobenzyl)-3,3-dimethyl-5-methoxy-2-indolinylidenemethyl)cyclobutenediylium-1,3-diolate (Compound 5);
vi) 2-(1-(5-carboxypentyl)-3,3-dimethyl-5-methoxy-2-indolinylidenemethyl)-4-(1-(3, 5-dinitrobenzyl)-3,3-dimethyl-5-methoxy-2-indolinylidenemethyl)cyclobutenediylium-1,3-diolate (Compound 6);
vii) 3-(5-carboxypentyl)-1-(2-(2-methoxyethoxy)ethyl-3-methyl-1,3-dihydro-2H-indol-2-ylidenemethyl-4-((1-(3, 5-dinitrobenzyl)-3,3-dimethyl-3H-indolium-2-yl)methylene)-3-oxocyclobut-1-en-1-olate (Compound 7); and
viii) 2-((3,3-dimethyl-5-sulfo-1-(4-sulfobutyl)-1,3-dihydro-2H-indol-2-ylidene)methyl)-4-(1-methyl-6-nitroquinolinium-2-yl)methylene)-3-oxocyclobut-1-en-1-olate (Compound 8)

EXAMPLES

The following examples describe assay procedures using recombinant adenoviral vectors for single 96 well plates of target cells. The present examples are provided for illustrative purposes only, and should not be interpreted in any way as limiting the scope of the invention as defined by the appended claims. All references provided below and elsewhere in the present specification are hereby included herein via reference.

1. Preparation of 2-(1-methyl-3,3-dimethyl-2-indolinylidenemethyl)-4-(1-(3,5-dinitrobenzyl)-3,3-dimethyl-2-indolinylidenemethyl)cyclobutenediylium-1, 3-diolate (Compound (1))

Compound (1)

1.1 Preparation of 1-(3,5-Dinitrobenzyl)-2,3,3-trimethyl-3H-indolium iodide

To 2,3,3-trimethylindolenine (1.64 g) was added 3,5-dinitrobenzyl iodide (3.71 g) and dichlorobenzene (15 ml). After heating to 90° C. for 6 hours the mixture was allowed to cool and the resultant precipitate removed by filtration. The solid was washed with dichlorobenzene (2×10 ml) and ether (2×50 ml). The material was dried in a vacuum oven to give the product as a yellow solid (2.69 g).

MALDI-TOF ($C_{18}H_{18}N_3O_4$ requires $M^+$ 340) 339, 340.

1.2 Preparation of Compound (1)

To 1-(3,5-dinitrobenzyl)-2,3,3-trimethyl-3H-indolium iodide (100 mg) was added 3-hydroxy-4-(1,3,3-trimethyl-1, 3-dihydroindol-2-ylidenemethyl)cyclobut-3-ene-1,2-dione (54 mg), pyridine (2.25 ml), acetic acid (2.25 ml) and acetic anhydride (0.5 ml). The mixture was heated to reflux for 6 hours and the solvent then stripped using rotary evaporation. The residue was partitioned between water and dichloromethane, and the organic phase sequentially washed with dilute aqueous sodium hydrogen carbonate solution and 1M HCl. The solvent was stripped and silica flash column chromatography performed (MeOH/DCM). The resulting material was further purified by reverse phase HPLC (CH$_3$CN/H$_2$O/TFA).

MALDI-TOF (C$_{34}$H$_{30}$N$_4$O$_6$ requires M$^+$ 590) 591.

2. Preparation of 2-(1-(5-carboxypentyl)-3,3-dimethyl-2-indolinylidenemethyl)-4-(1-(3,5-dinitrobenzyl)-3,3-dimethyl-2-indolinylidenemethyl)cyclobutenediylium--1,3-diolate (Compound (2))

Compound (2)

To 1-(3,5-dinitrobenzyl)-2,3,3-trimethyl-3H-indolium iodide (467 mg) was added 3,4-dihydroxy-3-cyclobuten-1,2-dione (110 mg), 1-(5-carboxypentyl)-2,3,3-trimethyl-3H-indolium iodide (354 mg), pyridine (4.5 ml), acetic acid (4.5 ml) and acetic anhydride (1 ml). The mixture was heated to reflux for 3 hours and the solvent then stripped using rotary evaporation. This crude material was subjected to silica flash column chromatography (eluted with MeOH/DCM). Fractions containing product were combined and stripped of solvent. The resulting material was further purified by reverse phase HPLC (CH$_3$CN/H$_2$O/TFA).

3. Preparation of 2-(1-(5-carboxypentyl)-3,3-dimethyl-2-benzindolinylidenemethyl)-4-(1-(3,5-dinitrobenzyl)-3,3-dimethyl-2-indolinylidenemethyl)cyclobutenediylium-1,3-diolate (Compound (3))

Compound (3)

3.1 Preparation of 3-(5-carboxypentyl)-1,1,2-trimethyl-1H-benzo[e]indolium iodide To 1,1,2-trimethyl-1H-benzo[e]indolenine (16.2 g) was added 6-bromohexanoic acid (31.2 g) and dichlorobenzene (50 ml). The mixture was heated at 110° C. for 136 hrs, cooled to ambient temperature, chilled upon ice and filtered. The filter cake was washed with dichlorobenzene (50 ml), diethyl ether (50 ml) and dried at 40° C. under a low vacuum to afford the title compound as a beige solid (25.38 g).

LCMS (C$_{21}$H$_{26}$NO$_2$ requires M$^+$ 324) 324.

3.2 Preparation of Compound (3)

To 1-(3,5-dinitrobenzyl)-2,3,3-trimethyl-3H-indolium iodide (132 mg) was added 3-(5-carboxypentyl)-1,1,2-trimethyl-1H-benzo[e]indolium iodide (114 mg), 3,4-dihydroxy-3-cyclobuten-1,2-dione (32 mg), pyridine (4.5 ml), acetic acid (4.5 ml) and acetic anhydride (1 ml). The mixture was heated to 90° C. for 4 hours and the solvent then stripped using rotary evaporation. Silica flash column chromatography was performed (EA/MeOH) and the relevant fractions combined and concentrated. The resulting material was further purified by reverse phase HPLC (CH$_3$CN/H$_2$O/TFA) to give 1.7 mg.

MALDI-TOF (C$_{43}$H$_{40}$N$_4$O$_8$ requires M$^+$ 740) 741.

4. Preparation of 2-(3-ethyl-6-nitro-2-benzothiazolinylidenemethyl)-4-(1-(2-(2-methoxyethoxy)ethyl)-3,3-dimethyl-2-indolinylidenemethyl)cyclobutenediylium-1,3-diolate (Compound (4))

Compound (4)

4.1 Preparation of 1-(2-(2-methoxyethoxy)ethyl)-2,3,3-trimethyl-3H-indolium bromide To 2,3,3-trimethylindolenine (1.59 g) was added 1-bromo-2-(2-methoxyethoxy)ethane (2.75 g) and dichlorobenzene (5 ml). The mixture was heated to 70° C. overnight. The volatiles were stripped and the material purified by HPLC.

MALDI-TOF (C$_{16}$H$_{24}$NO$_2$ requires M$^+$ 262) 263.

4.2 Preparation of 2-methyl-6-nitrobenzothiazole

2-Methylbenzothiazole (22 g) in conc. sulfuric acid (80 ml) was cooled to −5° C. A mixture of conc. sulfuric acid (12 ml) in conc. nitric acid (20 ml) was added so as to maintain the temperature below 5° C. (ca. 1.5 hours). After this time the mixture was allowed to warm to room temperature and the solution poured onto ice to give a yellow precipitate. The solid was removed by filtration and recrystallised from ethanol. After filtration the solid was washed with ethanol and dried in a vacuum oven to give 18 g of the desired product.

LCMS (C$_8$H$_6$N$_2$O$_2$S requires M$^+$ 194) 195.

4.3 Preparation of 3-ethyl-2-methyl-6-nitrobenzothiazolium iodide

To 2-methyl-6-nitrobenzothiazole (0.36 g) was added ethyl iodide (1.5 ml) and dichlorobenzene (20 ml). The mixture was heated to 120° C. for 2 days and then allowed to cool to room temperature. Ethyl acetate was added and the resulting precipitate removed by filtration. Drying in a vacuum oven gave the desired material (80 mg).

4.4 Preparation of Compound (4)

To 3-ethyl-2-methyl-6-nitrobenzothiazolium iodide (400 mg) was added 3,4-dihydroxy-3-cyclobuten-1,2-dione (128 mg), 1-(2-(2-methoxyethoxy)ethyl)-2,3,3-trimethyl-3H-indolium bromide (420 mg), pyridine (20 ml), acetic acid (18 ml) and acetic anhydride (8 ml). The mixture was heated to 120° C. for 4 hours and then allowed to cool to room temperature. The volatiles were stripped by rotary evaporation; the residue dissolved in DCM, and silica flash chromatography performed (DCM/EA/MeOH). The material was further purified by prep. TLC to give 23 mg.

LCMS ($C_{30}H_{31}N_3O_6S$ requires $M^+$ 561) 560.

5. Preparation of 2-(1-ethyl-3,3-dimethyl-5-methoxy-2-indolinylidenemethyl)-4-(1-(3,5-dinitrobenzyl)-3,3-dimethyl-5-methoxy-2-indolinylidenemethyl)cyclobutenediylium-1,3-diolate (Compound (5))

Compound (5)

5.1 Preparation of 5-methoxy-2,3,3-trimethyl-3H-indole

To 4-methoxyphenyl hydrazine hydrochloride (4.84 g) was added 3-methyl-2-butanone (6.4 ml) and acetic acid (45 ml). The mixture was heated to 100° C. for 2.5 hours after which time the solvent was removed by rotary evaporation. Flash column chromatography gave the product (4.66 g).

δH (270 MHz; CDCl$_3$) 1.3 (6H, s), 2.2 (3H, s), 3.8 (3H, s), 6.8 (2H, m), 7.4 (1H, m).

5.2 Preparation of 1-ethyl-5-methoxy-2,3,3-trimethyl-3H-indolium iodide

To 5-methoxy-2,3,3-trimethyl-3H-indole (1.9 g) was added iodoethane (5 ml) and 1,2-dichlorobenzene (10 ml). The mixture was heated to 80° C. for 4 hours after which time the precipitate removed by filtration and washed sequentially with dichlorobenzene and diethyl ether. Drying in a vacuum oven gave the product (3 g).

δH (270 MHz; CDCl$_3$) 1.6 (3H, t), 1.6 (6H, s), 3.1 (3H, s), 3.9 (3H, s), 4.7 (2H, q), 7.1 (2H, m), 7.7 (1H, m).

5.3 Preparation of 1-(3,5-dinitrobenzyl)-5-methoxy-2,3,3-trimethyl-3H-indolium iodide To 5-methoxy-2,3,3-trimethyl-3H-indole (1.90 g) was added 3,5-dinitrobenzyl iodide (4.62 g) and 1,2-dichlorobenzene (10 ml). The mixture was heated at 75° C. for 3 hours, during which time an orange solid separated. The mixture was then cooled in an ice bath and the solid fraction collected by filtration; it was washed sequentially with dichlorobenzene and diethyl ether and dried under vacuum to give the product (2.62 g).

δH (270 MHz; DMSO-d$_6$) 1.6 (6H, s), 2.9 (~3H, s), 3.85 (3H, s), 6.1 (2H, s), 7.1 (1H, dd), 7.55 (1H, d), 7.8 (1H, d), 8.65 (2H, s) and 8.8 (1H, s).

5.4 Preparation of Compound (5)

To 1-(3,5-dinitrobenzyl)-5-methoxy-2,3,3-trimethyl-3H-indolium iodide (250 mg) was added 3,4-dihydroxy-3-cyclobuten-1,2-dione (55 mg), 1-ethyl-5-methoxy-2,3,3-trimethyl-3H-indolium iodide (175 mg), pyridine (2.25 ml), acetic acid (2.25 ml) and acetic anhydride (0.5 ml). The mixture was heated to reflux for 5 hours and the solvent then removed using rotary evaporation. The crude material was partitioned between DCM and 1M HCl. The organic layer was further washed with water. Silica flash column chromatography was performed (DCM/MeOH) and the relevant fractions combined and concentrated. The resulting material was further purified by reverse phase HPLC (CH$_3$CN/H$_2$O/TFA).

MALDI-TOF ($C_{37}H_{36}N_4O_8$ requires $M^+$ 664) 665.

6. Preparation of 2-(1-(5-carboxypentyl)-3,3-dimethyl-5-methoxy-2-indolinylidenemethyl)-4-(1-(3,5-dinitrobenzyl)-3,3-dimethyl-5-methoxy-2-indolinylidenemethyl)cyclobutenediylium-1,3-diolate (Compound (6))

Compound (6)

6.1 Preparation of 1-(5-carboxypentyl)-5-methoxy-2,3,3-trimethyl-3H-indolium bromide To 5-methoxy-2,3,3-trimethyl-3H-indole (1.9 g) was added 6-bromohexanoic acid (3 g) and 1,2-dichlorobenzene (10 ml). The mixture was heated to 100° C. for 3 hours and then allowed to cool to room temperature. Diethyl ether was added and the precipitated material removed by filtration. Drying in a vacuum oven gave the product (3.12 g).

δH (270 MHz; CDCl$_3$) 1.4 (2H. m), 1.5 (6H, s), 1.6 (2H, m), 1.8 (2H, m), 2.2 (2H, m), 2.8 (3H, s), 3.8 (3H, s), 4.4 (2H, m), 7.1 (1H, m), 7.5 (1H, m), 7.9 (1H, m).

6.2 Preparation of Compound (6)

To 1-(3,5-dinitrobenzyl)-5-methoxy-2,3,3-trimethyl-3H-indolium iodide (500 mg) (see 5.3) was added 3,4-dihydroxy-3-cyclobuten-1,2-dione (14 mg), 1-(5-carboxypentyl)-5-methoxy-2,3,3-trimethyl-3H-indolium bromide (385 mg), pyridine (4.5 ml), acetic acid (4.5 ml) and acetic anhydride (1 ml). The mixture was heated to 110° C. for 4.5 hours and the solvent then removed using rotary evaporation. This crude material was partitioned between DCM and 1M HCl. The organic layer was further washed with water. Silica flash column chromatography was performed (DCM/MeOH) and the relevant fractions combined and concentrated. The resulting material was further purified by reverse phase HPLC ($CH_3CN/H_2O$/TFA).

MALDI-TOF ($C_{41}H_{42}N_4O_{10}$ requires $M^+$ 750) 751.

7. Preparation of 3-(5-carboxypentyl)-1-(2-(2-methoxyethoxy)ethyl-3-methyl-13-dihydro-2H-indol-2-ylidenemethyl-4-((1-(3,5-dinitrobenzyl)-3,3-dimethyl-3H-indolium-2-ylmethylene)-3-oxocyclobut-1-en-1-olate (Compound (7))

Compound (7)

7.1 Preparation of 3-(5-carboxypentyl)-1-(2-(2-methoxyethoxy)ethyl)-2,3-dimethyl-3H-indolium bromide To 6-(2,3-dimethyl-3H-indol-3-yl)hexanoic acid (100 mg) was added 1-bromo-2-(2-methoxyethoxy)ethane (1 ml) and the mixture heated to 90° C. overnight. On cooling diethyl ether (10 ml) was added and the material removed by filtration.

LCMS ($C_{21}H_{32}NO_4$ requires $M^+$ 362) 363.

7.2 Preparation of Compound (7)

To 3-(5-carboxypentyl)-1-(2-(2-methoxyethoxy)ethyl)-2,3-dimethyl-3H-indolium bromide was added squaric acid (44 mg), 1-(3,5-dinitrobenzyl)-2,3,3-trimethyl-3H-indolium iodide (177 mg), pyridine (4.5 ml), acetic acid (4.5 ml) and acetic anhydride (1 ml). The mixture was heated to 80° C. overnight. On cooling preparative HPLC was performed to give the desired material.

LCMS ($C_{43}H_{46}N_4O_{10}$ requires $M^+$ 778) 779.

8. Preparation of the acetoxymethyl ester derivative of Compound (7)

To 3-(5-carboxypentyl)-1-(2-(2-methoxyethoxy)ethyl-3-methyl-1,3-dihydro-2H-indol-2-ylidenemethyl-4-((1-(3,5-dinitrobenzyl)-3,3-dimethyl-3H-indolium-2-yl)methylene)-3-oxocyclobut-1-en-1-olate (14 mg) was added acetonitrile (3 ml), Hunigs base (32 μl) and bromomethyl acetate (9 ul). After stirring at room temperature for 2 hours, HPLC was performed to give the desired material (8 mg).

LCMS ($C_{46}H_{50}N_4O_{12}$ requires $M^+$ 850) 851.

9. Preparation of the ethyl ester derivative of Compound (7)

To ethanol (10 ml) was added acetyl chloride (1 ml) followed by 3-(5-carboxypentyl)-1-(2-(2-methoxyethoxy)ethyl-3-methyl-1,3-dihydro-2H-indol-2-ylidenemethyl-4-((1-(3,5-dinitrobenzyl)-3,3-dimethyl-3H-indolium-2-yl)methylene)-3-oxocyclobut-1-en-1-olate (2 mg). The mixture was stirred at room temperature for 5 hours, after which time the volatiles were stripped in vacuo.

LCMS ($C_{45}H_{50}N_4O_{10}$ requires $M^+$ 806) 807.

10. Preparation of -2-((3,3-dimethyl-5-sulfo-1-(4-sulfobutyl)-1,3-dihydro-2H-indol-2-ylidene)methyl)-4-((1-methyl-6-nitroquinolinium-2-yl)methylene)-3-oxocyclobut-1-en-1-olate (Compound (8))

Compound (8)

10.1 Preparation of 1,2-dimethyl-6-nitroquinolinium iodide

2-Methyl-6-nitroquinoline (0.5 g, 2.66 mmol) and iodomethane (1 ml, 16 mmol) were heated together in acetonitrile (10 ml) at reflux for 48 hrs. The mixture was cooled to room temperature and a grey material crystallised out of solution and was filtered off. This was shown to be starting material. The filtrate was diluted with ethyl acetate (200 ml) to give a yellow/green precipitate. The product was filtered off, washed with ethyl acetate and then dried under vacuum. The product was obtained as a yellow/green solid (147 mg, 16.8%).

LCMS ($C_{11}H_{11}N_2O_2$ requires $M^+$ 203) single component $M^1$ 203.

10.2 Preparation of 2,3,3-trimethyl-5-sulfo-1-(4-sulfobutyl)-3H-indolium, potassium salt 2,3,3-Trimethylindolenine-5-sulfonate, potassium salt (6 g, 21.6 mmol) and 1,4-butanesultone (55 ml) were heated together, under nitrogen, at 90° C. for 24 hrs. On cooling the reaction mixture was diluted with ethyl acetate and the resultant solid filtered off, washed with ethyl acetate and dried under vacuum. The product was isolated as a pale pink solid (10.3 g). The product was characterised by $^1$H NMR ($CD_3OD$).

10.3 Preparation of Compound (8)

1,2-Dimethyl-6-nitro-quinolinium iodide (100 mg, 0.30 mmol), 3,4-dihydroxy-3-cyclobutene-1,2-dione (34.5 mg, 0.30 mmol) and 2,3,3-trimethyl-5-sulfo-1-(4-sulfobutyl)-3H-indolium, potassium salt (124 mg, 0.30 mmol) were heated together in a mixture of pyridine (3 ml), acetic acid (3 ml) and acetic anhydride (2 ml) at 120° C. for 1 hr. The reaction mixture is seen to turn to a dark green/blue colour. On cooling the reaction mixture was poured into ethyl acetate to precipitate the products. The products were filtered off and mixture purified by RP HPLC using eluent mixtures of water/acetonitrile/0.1% TFA.

The product was obtained as a dark blue solid (14 mg).

LCMS ($C_{30}H_{30}N_3O_{10}S_2$ requires $M^+$ 656) $ES^-$ gives $(M-H)2^-$ reconstruction gives $M^-$ at 654.

11. A Comparative Study of a Nitro-substituted Squaraine Dye (Compound (1)) with Nitro-substituted Cyanine Dyes (Compounds (i) and (iii)) as Substrates in a Nitroreductase Gene Reporter Assay A reporter construct containing the NF-κB response element upstream of the NTR gene was constructed in pDC511 (Admax™). The reporter was packaged with Ad5 genomic DNA in helper cells, HEK293, and replication incompetent Adenovirus rescued.

HeLa cells were subcultured for twenty-four hours prior to viral transduction and incubated overnight at 37° C. in a humidified atmosphere of 5% $CO_2$ in Dulbecco's Modified Eagles medium containing 10% foetal calf serum+2 mM L-glutamine. After the overnight incubation, the cells were detached from each flask with trypsin, pooled to produce a suspension of cells and the cell concentration determined. The HeLa cell suspension was mixed with virus at a predetermined multiplicity of infection (MOI) in a sufficient minimal volume of complete medium to cover the base of a tissue culture flask; typically 15 ml for $10^6$ cells in a T75 $cm^2$ Costar flask. The cell/virus suspension was returned to the incubator and left overnight at 37° C. in a humidified atmosphere of 5% $CO_2$. The following day the medium was removed from each flask and the cell monolayer rinsed with 5-10 ml PBS. The cells were detached with trypsin and pooled to produce a suspension of transduced cells; the concentration of the cell suspension was determined and adjusted to $5.0 \times 10^4$ cells per ml. 200 μl of this cell suspension was dispensed into each well of a 96-well microtitre plate; $\approx 10^4$ cells per well. All plates were incubated overnight at 37° C. in a humidified atmosphere of 5% $CO_2$. The overnight medium was replaced with 200 μl PBS. The PBS was removed from each well and replaced with TNFα agonist in serum free Dulbecco's Modified Eagles medium (100 ng/ml, 90 μl) or control (90 μl serum free medium) was added to replicate wells. Plates were returned to the incubator at 37° C. in an atmosphere of 5% $CO_2$ for 2 hours. After this time, 10 μl of a 10 μM solutions of Compounds (i) and (iii) (nitro-cyanine dyes) and Compound (1) (nitro-squaraine dye) were dispensed individually into replicate wells and plates returned to 37° C. in a humidified atmosphere of 5% $CO_2$. The fluorescence signal was monitored over time by means of a Tecan "Ultra" fluorimeter. All substrates were measured under identical conditions to avoid instrument artifacts.

Figure 1A:
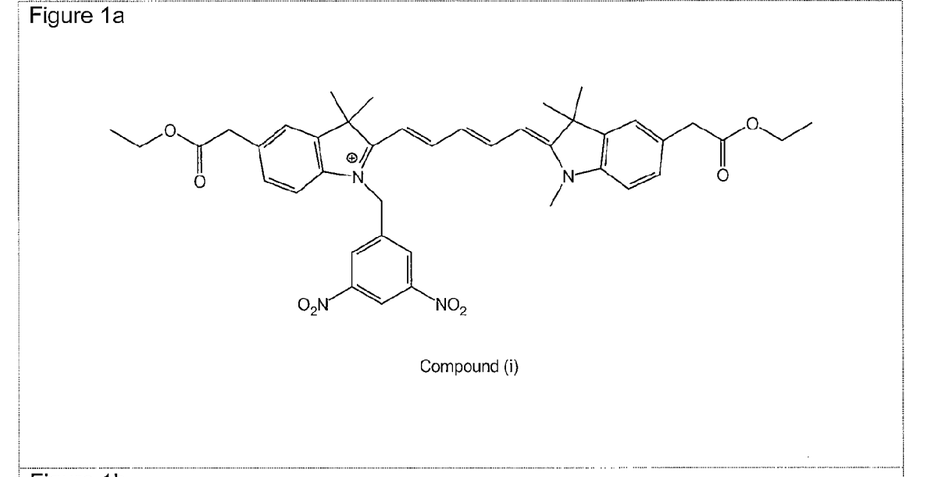
FIGS. 1a and 1b show the molecular structures of two nitro-substituted cyanine type dyes, Compounds (i) and (iii) compared with a nitro-substituted squaraine dye of the invention (Compound (1)) as substrates in a nitroreductase gene reporter assay, as in Example 11.
Figure 1B:
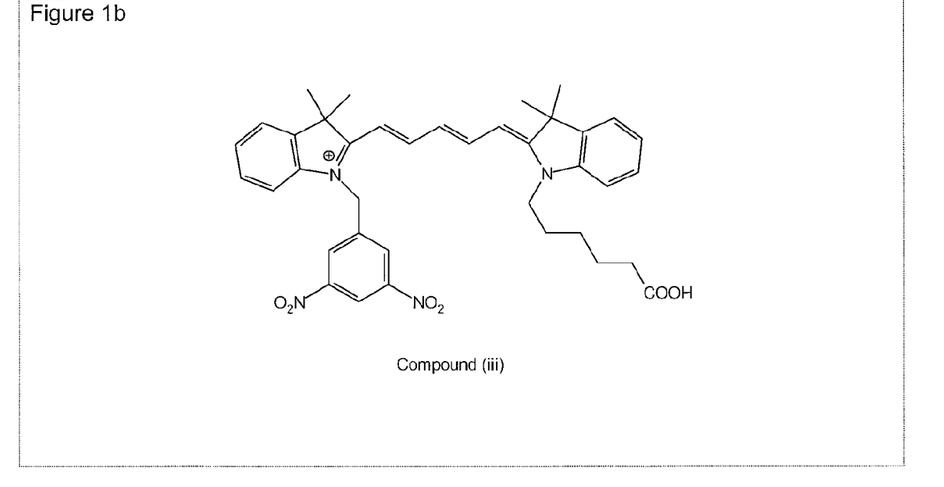
Figure 2A:
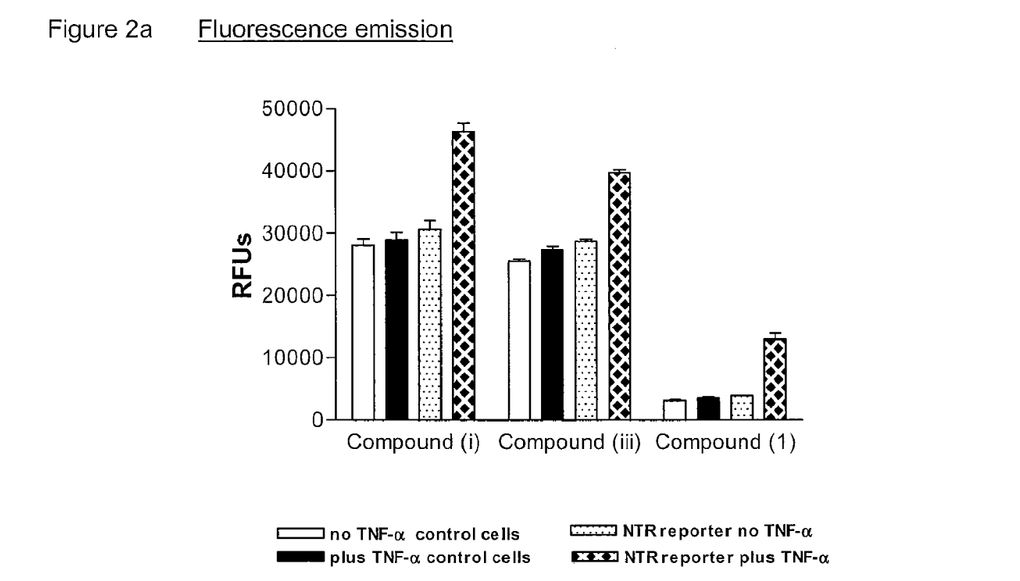
FIGS. 2a and 2b illustrate the comparison of two nitro-substituted cyanine dyes, Compounds (i) and (iii) compared with a nitro-substituted squaraine in an NTR gene reporter assay (Compound (1)).
Figure 2B:
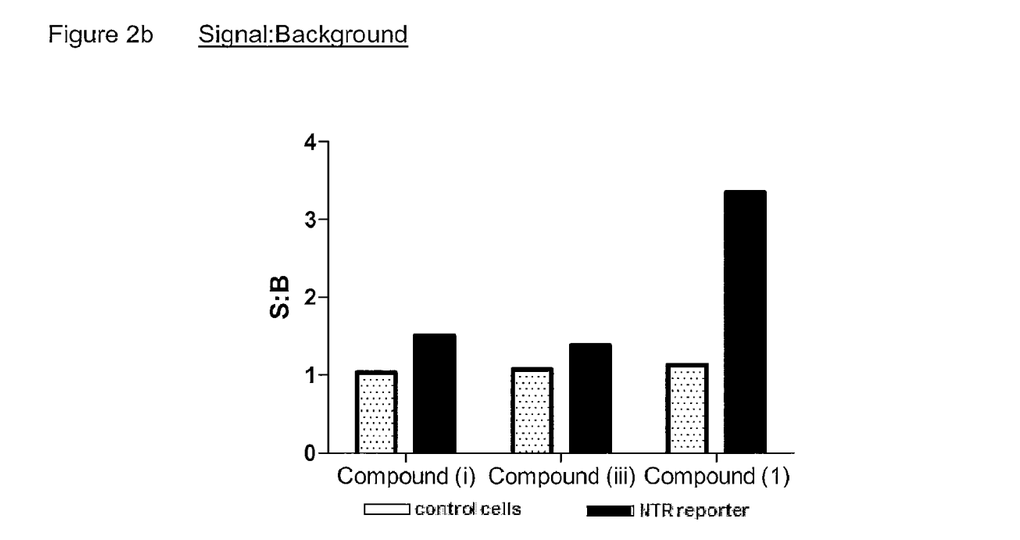

FIG. 2 compares the performance of a nitro group-containing squaraine dye (Compound (1) with nitro group-containing cyanine dyes (Compounds (i) and (iii)). The signal to background ratio for Compound (1) was 3:1 (compared with 1.3:1 for Compound (i), clearly demonstrating a reduction in background fluorescence combined with a similar increase in fluorescence signal.

Figure 3A:
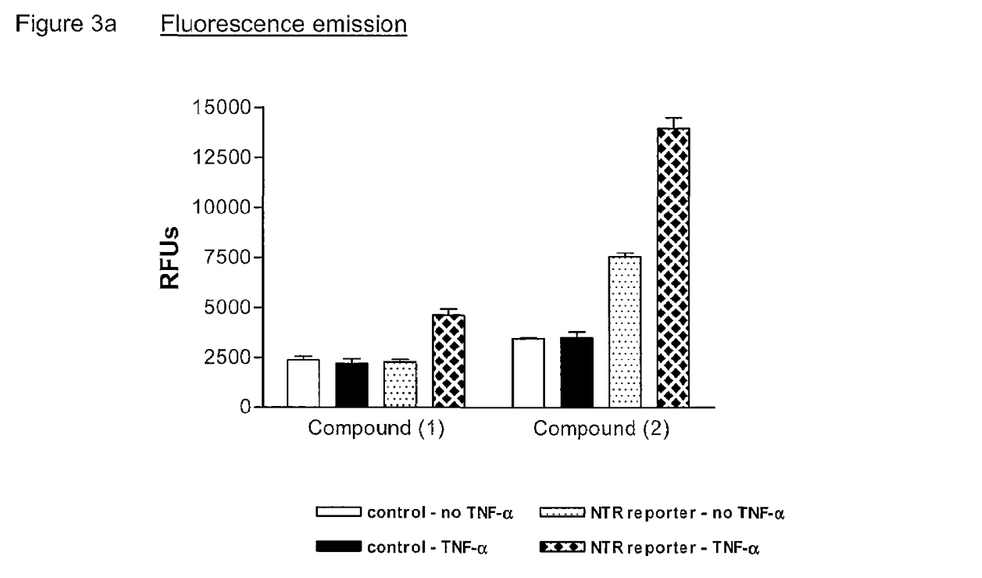
FIGS. 3a and 3b are a comparative study of nitro-substituted squaraine dyes (Compounds (1) and 2) as substrates in a nitroreductase gene reporter assay.
Figure 3B:
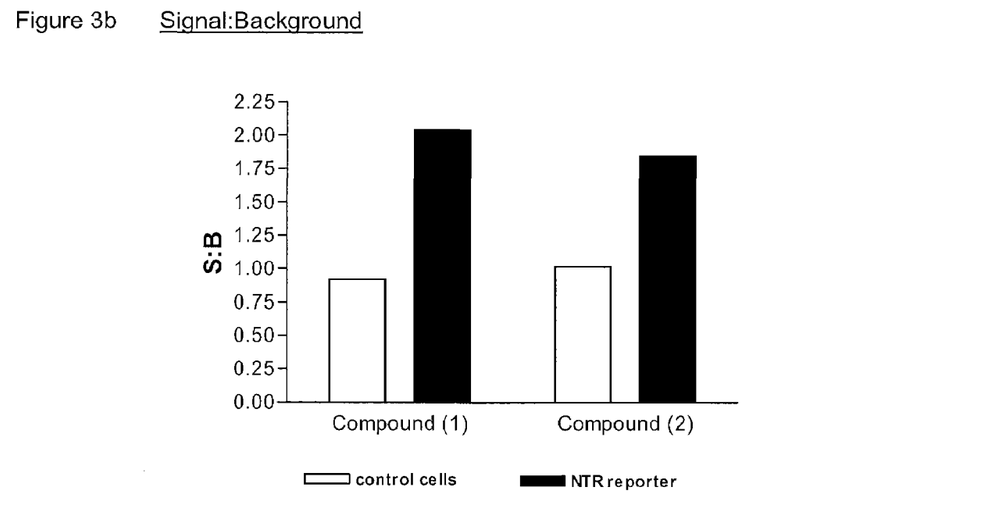

12. A Comparative Study of Nitro-substituted Squaraine Dyes (Compounds (1) and (2)) as Substrates in a Nitroreductase Gene Reporter Assay Using the same methodology as that described in Example 11, HeLa cells were transduced with the adenoviral NF-κB reporter system. At the appropriate time Compounds (1) and (2) were added individually to replicate wells. The fluorescence signal was monitored over time on a Tecan Ultra fluorimeter and data presented in FIG. 3.

Compound (2) clearly shows a significant increase in assay signal when compared to Compound (1) in the presence of the agonist, TNF-α. Compound (2) was also capable of detecting basal transcriptional activity in the control sample cells containing the reporter. This basal activity is the difference in signal between cells containing the NF-κB reporter but no agonist and mock transduced cells. Compound (1) was not sensitive enough to detect this low level activity. The improvements in assay sensitivity are believed to be a direct consequence of the availability of the improved compounds within the cell. Thus, Compound (2) is thought to be available in the cell cytoplasm which is also the same compartment as the expressed reporter protein. Microscopic imaging of the assay plates have produced cells with intense red cytoplasm staining following NTR expression.

The data from FIGS. 2 and 3 illustrate that the improved properties of the nitro-substituted squaraine dye (Compound (2)) are a result of introducing both the squarylium moiety into the dye and the addition of the hexanoic acid group. The presence of the hexanoic acid group in Compound (iii), nitro-substituted cyanine dye, was not sufficient to alter the cellular localisation of Compound (i), nor its performance in the NTR assay.

13. Localisation of Compound (2) in HeLa Cells

HeLa cells were plated at 120,000 per dish and incubated overnight at 37° C. In Dulbecco's Modified Eagles medium containing 10% foetal calf serum +2 Mm L-glutamine. Overnight medium was removed and replaced with 2 ml of serum free medium containing 1 μM Compound (2). Dishes were returned to the incubator for 2 hours before imaging on a Zeiss Confocal Microscope.

Figure 4:
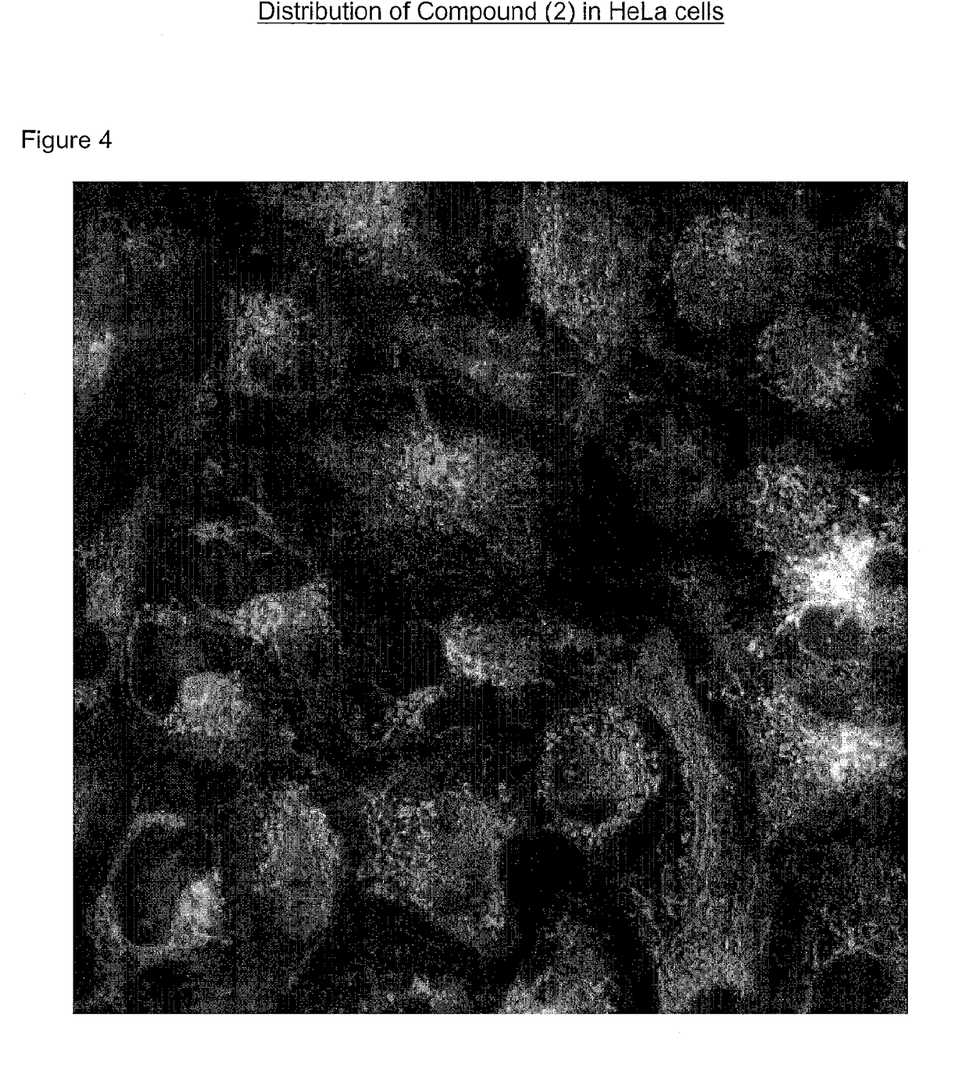
FIG. 4 shows the distribution of Compound (2) in HeLa cells.

FIG. 4 shows the uptake and distribution of Compound (2) in HeLa cells. There was no evidence to indicate that Compound (2) was sequestered to organelles. Although there is evidence of background labelling of cell structures, this does not compromise the assay performance.

Figure 5A:
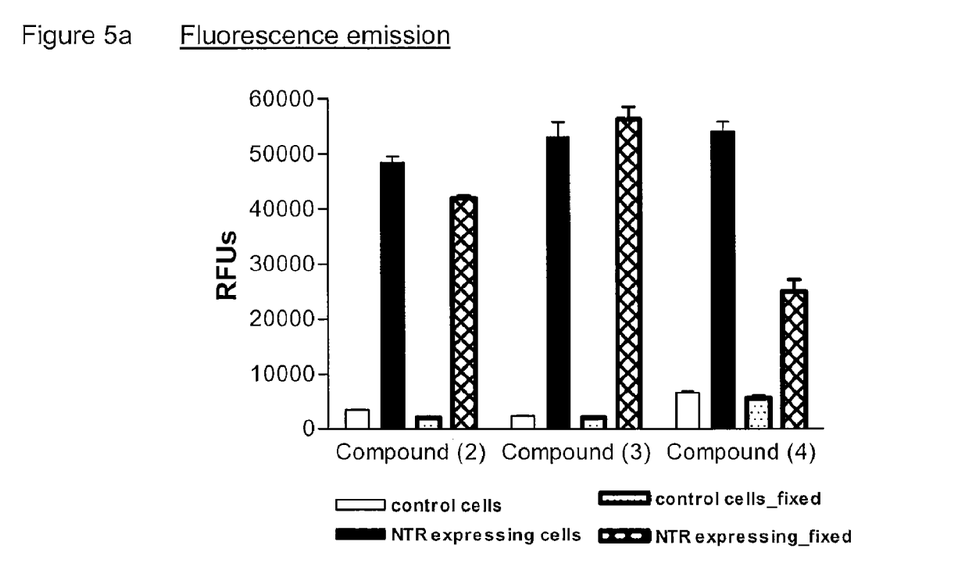
FIGS. 5a and 5b show the evaluation of Compounds (2), (3) and (4) as nitroreductase substrates in live cell NTR assays.
Figure 5B:
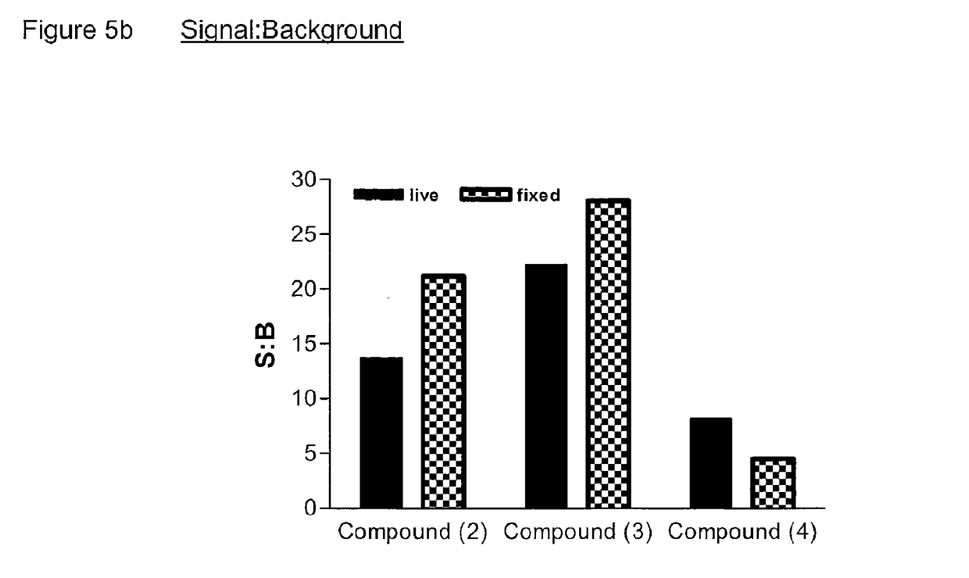

14. Evaluation of Compounds (2), (3) and (4) as Nitroreductase Substrates in live cell NTR assays Further examples of the utility of nitro-substituted squaraine dyes (Compounds (2), (3) and (4)) as nitroreductase substrates are shown in live cell NTR assays, FIG. 5. The data presented in FIG. 5 for Compound (3) shows that a squaraine dye substrates that omits at longer wavelength may be obtained by extending the conjugation system of the dye. The presence of the hexanoic group increases the retention properties of the probe within the cell as demonstrated by the fixation of cells. Compounds (2) and (3) show very little decrease in signal following fixation while Compound (4) has lost almost 50% of the signal post-fixation.

15. Example of Shift in Absorption Maximum After Action of NTR Upon a Substrate Compound (8) in DMSO (1 mMol) (4 µl) was diluted into PBS buffer (0.01M) (1.76 ml). The UV/Vis spectrum of the solution was measured. The substrate has an absorbance maximum at 682 nm AU=0.22. To the solution was added NADH (0.01M in PBS) (200 µl) and NTR enzyme (446 ng/ml, 37 µl) the mixture was leave to stand at room temperature for 30 mins. After this time, the absorbance spectrum was re-measured. A new absorbance maximum at 621 nm, AU=0.17 is observed.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method for detecting nitroreductase enzyme activity in a composition comprising:
   i) mixing said composition under conditions to promote nitroreductase activity with a dye molecule; and
   ii) measuring a change in an optical property of said dye molecule wherein said change is a measure of the amount of nitroreductase activity;
   wherein said dye molecule is a squaraine dye comprising at least one $NO_2$ group.

2. The method of claim 1, wherein said composition comprises at least one cell or a cell extract.

3. The method of claim 1, wherein said method is conducted in the presence of a test agent whose effect on nitroreductase enzyme activity is to be determined.

4. A method which comprises:
   i) contacting a host cell with a dye molecule wherein said host cell has been transfected with a nucleic acid molecule comprising expression control sequences operably linked to a sequence encoding a nitroreductase; and
   ii) measuring a change in an optical property of said dye molecule wherein said change is a measure of the amount of nitroreductase activity;
   wherein said dye is a squaraine dye comprising at least one $NO_2$ group.

5. The method of claim 1 or 4, wherein said change in an optical property is an increase in the fluorescence intensity of the dye molecule, whereby said increase is a measure of the amount of nitroreductase activity.

6. The method of claim 1 or 4, wherein said squaraine dye is of formula (I):

(I)

wherein:
$R^3$ is attached to the $Z^1$ ring structure and $R^4$ is attached to the $Z^2$ ring structure;

$Z^1$ and $Z^2$ independently represent a phenyl or a naphthyl ring system;

X and Y are the same or different and are selected from oxygen, sulphur, —CH=CH— and the group:

groups $R^1$ and $R^2$ are independently selected from $C_1$-$C_4$ alkyl, —$(CH_2)_n$—P, —$\{(CH_2)_2$—$O\}_p$—$R^6$ and the group W; where P is selected from $COOR^7$, $SO_3^-$ and OH, W is mono- or di-substituted nitrobenzyl, $R^6$ is methyl or ethyl, $R^7$ is selected from H, $C_1$-$C_4$ alkyl and $CH_2OC(O)R^8$, where $R^8$ is methyl, or t-butyl, n is an integer from 1 to 10, and p is an integer from 1to 3;

groups $R^3$ and $R^4$ are independently selected from hydrogen, $NO_2$, halogen, $SO_3^-$, $C_1$-$C_4$ alkoxy and —$(CH_2)_m$—$COOR^7$; where $R^7$ is hereinbefore defined and m is 0 or an integer from 1 to 5;

$R^5$ is $C_1$-$C_6$ alkyl optionally substituted with $COOR^7$, $SO_3^-$, or OH; where $R^7$ is hereinbefore defined; and at least one of groups $R^1$, $R^2$, $R^3$ and $R^4$ comprises at least one $NO_2$ group.

7. The method of claim 6, wherein said dye is, or is rendered, cell permeable.

8. The method of claim 1 or 4, wherein said squaraine dye is a compound selected from dyes of formula:

(II)

(III)

(IV)

wherein:
X and Y are the same or different and are selected from oxygen, sulphur, —CH=CH— and the group:

wherein $R^5$ is hereinbefore defined;

at least one of groups $R^1$ and $R^2$ is the group W; where W is hereinbefore defined;

any remaining group $R^1$ or $R^2$ is selected from $C_1$-$C_4$ alkyl, —$(CH_2)_n$—P and —$\{(CH_2)_2$—O$\}_p$—$R^6$; where P is selected from COOR$^7$, SO$_3^-$ and OH, $R^6$ is methyl or ethyl, $R^7$ is selected from H, $C_1$-$C_4$ alkyl and CH$_2$OC(O)R$^8$, where $R^8$ is methyl, or t-butyl, n is an integer from 1 to 10 and p is an integer from 1 to 3; and groups $R^3$ and $R^3$ are independently selected from hydrogen, halogen, SO$_3^-$, $C_1$-$C_4$ alkoxy and —$(CH_2)_m$—COOR$^7$; where $R^7$ is hereinbefore defined and m is 0 or an integer from 1 to 5.

9. The method of claim 8, wherein one of groups $R^1$ and $R^2$ is selected from group W where W is selected from:

remaining $R^1$ or $R^2$ is selected from methyl and ethyl, or is the group —$(CH_2)_n$—COOR$^7$ where $R^7$ is selected from H, $C_1$-$C_4$ alkyl and CH$_2$OC(O)R$^8$, where $R^8$ is methyl, or t-butyl, n is an integer from 1 to 10, preferably 5 or 6.

10. The method of claim 9, wherein W is the group:

and remaining $R^1$ or $R^2$ is hereinbefore defined.

11. The method of claim 1 or 4, wherein said squaraine dye is a compound of formula:

wherein:

X and Y are the same or different and are selected from oxygen, sulphur, —CH═CH— and the group:

wherein $R^5$ is hereinbefore defined;

groups $R^1$ or $R^2$ are independently selected from $C_1$-$C_4$ alkyl, —$(CH_2)_n$—P and —$\{(CH_2)_2$—O$\}_p$—$R^6$; where P is selected from COOR$^7$, SO$_3^-$ and OH, $R^6$ is methyl or ethyl, $R^7$ is selected from H, $C_1$-$C_4$ alkyl and CH$_2$OC(O)R$^8$, where $R^8$ is methyl, or t-butyl, n is an integer from 1 to 10 and p is an integer from 1 to 3;

at least one of groups $R^3$ and $R^4$ is NO$_2$; and any remaining group $R^3$ or $R^4$ is selected from hydrogen, SO$_3^-$, $C_1$-$C_4$ alkoxy and —$(CH_2)_m$—COOR$^7$; where $R^7$ is selected from H, $C_1$-$C_4$ alkyl and CH$_2$OC(O)R$^8$, where $R^8$ is methyl, or t-butyl, and m is 0 or an integer from 1 to 5.

12. A method for screening for a test agent whose effect upon nitroreductase gene expression is to be determined, said method comprising:

a) performing the method of claim 4 in the absence and in the presence of said test agent; and b) determining the amount of nitroreductase gene expression in the absence and in the presence of said agent;

wherein a difference between the amount of nitroreductase gene expression in the absence and in the presence of said agent is indicative of the effect of said agent on nitroreductase gene expression.

13. A method of screening for a test agent whose effect upon nitroreductase gene expression is to be determined, said method comprising:

a) performing the method of claim 4 in the presence of said agent; and b) comparing the amount of nitroreductase gene expression with a control value for the amount of nitroreductase gene expression in the absence of the test agent.

14. The method of claim 13, wherein said control value is stored electronically in a database or other electronic format.

* * * * *